(12) United States Patent
Chen et al.

(10) Patent No.: US 11,304,893 B2
(45) Date of Patent: Apr. 19, 2022

(54) LOW POWER, CHEMICALLY AMPLIFIED, ELECTRICALLY REMOVABLE BARRIER

(71) Applicant: CALIFORNIA INSTITUTE OF TECHNOLOGY, Pasadena, CA (US)

(72) Inventors: Samson Chen, Pasadena, CA (US); Axel Scherer, Pasadena, CA (US); Richard Daniel Smith, Jr., Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 385 days.

(21) Appl. No.: 16/044,124

(22) Filed: Jul. 24, 2018

(65) Prior Publication Data
US 2019/0060218 A1    Feb. 28, 2019

Related U.S. Application Data

(60) Provisional application No. 62/536,062, filed on Jul. 24, 2017.

(51) Int. Cl.
*A61J 1/14*    (2006.01)
*A61K 9/00*    (2006.01)
(Continued)

(52) U.S. Cl.
CPC ........ *A61K 9/0009* (2013.01); *A61B 5/14532* (2013.01); *A61B 5/4839* (2013.01); *A61B 5/686* (2013.01); *A61J 1/1412* (2013.01); *A61J 1/1468* (2015.05); *A61K 9/0024* (2013.01); *A61K 9/0097* (2013.01)

(58) Field of Classification Search
CPC .. A61K 9/0009; A61K 9/0024; A61K 9/0097; A61J 1/1412; A61J 1/1468; A61B 5/14532; A61B 5/4839; A61B 5/686
See application file for complete search history.

(56) References Cited

U.S. PATENT DOCUMENTS 4,902,278 A    2/1990    Maget et al.
5,366,454 A    11/1994   Currie et al.
(Continued)

FOREIGN PATENT DOCUMENTS

EP    1688132 A2    8/2006
WO    95/05452 A2    2/1995
(Continued)

OTHER PUBLICATIONS

International Search Report for International Application No. PCT/US2018/043558 filed Jul. 24, 2018 on behalf of California Institute of Technology. dated May 1, 2019. 4 pages.
(Continued)

*Primary Examiner* — Kai H Weng
(74) *Attorney, Agent, or Firm* — Steinfl + Bruno LLP

(57) ABSTRACT

An implantable device contains a drug or biosensing compound, protected from the external environment within a human body by several barriers which are broken upon activation of the device through electrothermal, chemical, and mechanical processes. The device allows accurate and repeated dosing within a human body, thus reducing the number of implantation procedures required. This device extends the lifetime of a biosensor, reducing the number of implantation procedures required.

21 Claims, 6 Drawing Sheets

(51) Int. Cl.
*A61B 5/145* (2006.01)
*A61B 5/00* (2006.01)

(56) References Cited

U.S. PATENT DOCUMENTS

| | | |
|---|---|---|
| 7,410,616 B2 | 8/2008 | Santini, Jr. et al. |
| 7,604,628 B2* | 10/2009 | Santini, Jr. ............ A61K 9/0009 604/890.1 |
| 2002/0183721 A1* | 12/2002 | Santini, Jr. ............ A61K 9/0097 604/890.1 |
| 2005/0143715 A1 | 6/2005 | Cima et al. |
| 2008/0302659 A1 | 12/2008 | Sheppard, Jr. et al. |
| 2016/0050750 A1* | 2/2016 | Rogers .................. H05K 3/285 361/767 |
| 2016/0299093 A1 | 10/2016 | Gilbert |
| 2021/0322300 A1 | 10/2021 | Chen et al. |

FOREIGN PATENT DOCUMENTS

| | | |
|---|---|---|
| WO | 98/00107 A2 | 1/1998 |
| WO | 01/64344 A2 | 9/2001 |
| WO | 2004/022033 A1 | 3/2004 |
| WO | 2011/046443 A1 | 4/2011 |
| WO | 2012/121691 A1 | 9/2012 |

OTHER PUBLICATIONS

Written Opinion for International Application No. PCT/US2018/043558 filed Jul. 24, 2018 on behalf of California Institute of Technology, dated May 1, 2019. 7 pages.

Santini, John T., Michael J. Cima, and Robert Langer. "A controlled-release microchip." Nature, vol. 397, (Jan. 28, 1999): 335-338.

Extended European Search Report for EP Application No. 18854735.0 filed on Feb. 21, 2020, on behalf of California Institute of Technology. dated May 26, 2021. 9 Pages.

* cited by examiner

LOW POWER, CHEMICALLY AMPLIFIED, ELECTRICALLY REMOVABLE BARRIER

CROSS REFERENCE TO RELATED APPLICATIONS

The present application claims priority to U.S. Provisional Patent Application No. 62/536,062, filed on Jul. 24, 2017, the disclosure of which is incorporated herein by reference in its entirety.

STATEMENT OF INTEREST

This invention was made with government support under Grant No. HR0011-15-2-0050 awarded by DARPA. The government has certain rights in the invention.

TECHNICAL FIELD

The present disclosure relates to controllable activation devices. More particularly, it relates to a low power, chemically amplified, electrically removable barrier.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
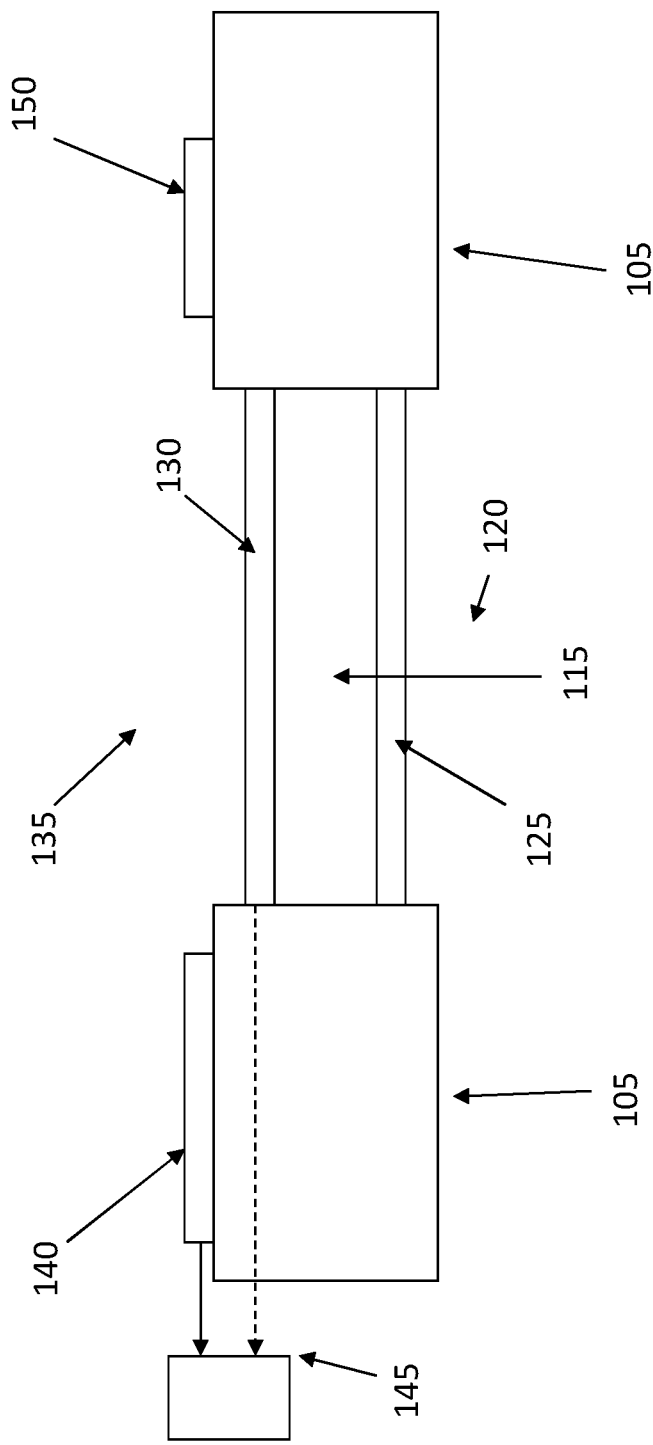
FIG. 1 illustrates an exemplary barrier arrangement.

In a first aspect of the disclosure, a device is described, the device comprising: a container having an opening; a plurality of barriers closing the opening; a chemical compound or biological material within the container, wherein: the device is configured to be implantable within a human body or other organism, and the plurality of barriers are configured to electrochemically or electrothermally dissolve, upon application of an electric potential or current to at least one barrier of the plurality of barriers, thereby allowing interaction between the chemical compound or biological material and the human body or other organism.

DETAILED DESCRIPTION

In a variety of applications, in particular with reference to implantable healthcare devices, there is often a need to temporarily separate pre-packaged chemical compounds and biological materials within the device from the surrounding environment. The separation generally needs to be maintained for a certain amount of time or until a certain condition is met, after which the chemical and biological compounds are allowed to interact with the environment on the other side of the separation. For example, a drug may be sealed within an implantable device, and released into the surrounding tissue after a specified amount of time. In certain applications, the amount of time needs to be controlled, for example electrically. In drug delivery devices, this mode of delivery entails keeping medication separate from the human body (or body of another organism) until it has been determined that dosing is required. This medication may include, for example, insulin, birth control hormones, or other medications requiring continuous dosing, dosing adjusted based on a measurement, or dosing triggered by a measurement. Alternatively, a local chemotherapeutic or anticoagulant may be released on the condition of local tumor recurrence or initiation of heart attack symptoms.

In implantable biosensors, the devices consist of interface materials and sensors capable of transducing the measurement of biologically relevant parameters. For example, implantable glucose sensors typically contain a crosslinked layer of glucose oxidase, an enzyme, deposited on top of an electrochemical sensor. This configuration allows for the continuous, quantitative, and specific measurement of glucose in the body. By changing the enzyme, other small molecules of medical significance may be measured, such as, for example, lactate or xanthine. Other types of biological compounds, such as thrombin, insulin, RNA and other macromolecules, may be measured using aptamer binding sensors or other techniques known to the person of ordinary skill in the art. However, these sensor types degrade very quickly in the environment of the human body, either due to degradation of the sensor material itself or attack from the immune system. For example, state-of-the-art implantable glucose sensors only function for two weeks in the body, despite having a lifetime of months in vitro. Therefore, a controlled interaction between the sensor and the environment is advantageous. In a method similar to controlled drug release, controlled exposure of biosensors can be carried out by retaining a limited-life sensing membrane to separate the sensor from the human body and immune system, until measurements need to be made.

For implantable devices it is generally desired to reduce the non-functional size of the device and extend the time duration during which the devices remain operable. If a device remains operable for a longer period of time, the discomfort of more frequent implantations of replacement devices can be avoided. If a device is made smaller, then the implantation procedure itself will have less risk and cause less discomfort. In the drug delivery market, the size of most long-term, implantable drug delivery devices is largely limited by their power source. For example, a current implantable drug delivery system which can be electrically actuated relies on electrothermally destroying a metal barrier separating a drug from the body. In other words, an electric current, powered by the device, generates thermal power to melt and destroy the metallic barrier. As it is known to the person of ordinary skill in the art, metals normally heat up when electric current flows through them.

The metal barrier keeps the contained compounds from contacting the surround environment, such as a human body in an implantable device. These existing devices typically require energy storage capable of supplying at least one Watt of power, in order to expose a prepackaged drug. The current is applied on demand to destroy the metal barrier and release the drug. This high power requirement makes it a significant challenge to wirelessly power such drug delivery implants, and puts a minimum size limit on the implant, due to the size required for a battery or other energy storage components.

Similar power issues limit the use of electrothermal barriers for implantable biosensors. Many biosensors contain chemically sensitive membranes which can easily be damaged by the body's immune response after implantation, which typically includes short-term damage from reactive oxygen species generated by the immune system, and long-term encapsulation of the device by scar tissue. By using a controllably degradable barrier, the sensitive membrane can be protected from exposure to the human body's immune system. Protection from the immune response improves the implant's lifetime. Electrically controlling exposure to the sensing membrane permits staggering of multiple membranes in a single device, drastically increasing the time required between re-implantations of implantable biosensor devices. For example, in glucose biosensors, the current state-of-the-art two-week lifetime can be extended into months using the technique described in the present disclosure. By staggering, multiple doses of a drug, or different drugs, can be released in succession as each are released one at a time by activating their respective barriers.

Another existing technique involves using gold barriers, as described in Santini et al., Nature 397.6717 (1999): 335-338, the disclosure of which is incorporated herein by reference in its entirety. In this type of drug delivery device, a microfabricated well containing a drug is covered by a relatively thin gold film. In the presence of chloride ions, typically present in all biological fluids, a range of electrical potentials applied to the barrier will dissolve the gold barrier into the solution, eventually exposing the drug covered by the gold film. The gold film needs to be relatively thick, of the order of hundreds of nanometers or more, to ensure a completely sealed and robust protection of the contents of the well (e.g. a drug). The power requirements to apply a potential which causes the electrochemical dissolution of the gold barrier are not as severe as for the case with electrothermal methods that destroy a barrier through a heat-generating current. However, the total energy required to fully open up the membrane can remain impractically large for implantable devices. Additionally, the rate at which the reaction occurs is dictated by the reaction between gold and chloride, which is typically fixed for a given environment (such as the human body). In certain circumstances, this specific rate may be too slow, given the thickness of the film typically required to protect the chemical compounds to be delivered (e.g. a drug). Additionally, the gold film does not always uniformly dissolve, which could result in large undissolved pieces of gold which impede delivery of the contained drug.

The present disclosure describes an alternative barrier design containing two, three, or more different types of materials. The method described herein permits electrical removal of a separating barrier with high speed, low power, and low total energy requirements, while maintaining long barrier lifetime and impermeability. Compared to the Amperes typically required in current implantable drug delivery devices making use of electrothermal barriers, less than 1 microAmpere is sufficient to open barriers of a similar size. In some situations this technique can, in fact, even generate energy for the operation of the device.

FIG. 1 illustrates an exemplary embodiment of the devices of the present disclosure. The first layer of the barrier (130), immediately exposed to the fluid environment (135) on one side of the barrier, is selected to be highly stable and non-reactive, but can be electrochemically removed. Gold is an excellent choice, as it is a biocompatible, noble metal, but other non-reactive materials may be used. As described earlier, gold is relatively stable in most implanted environments, but will controllably dissolve away in the presence of chloride ion when a specific range of electrical potentials are applied to the metal. The electrical potential can be determined given the chemical environment of the implant, and the type of reference electrode the potential is applied relative to. The metal barrier layers can be fabricated by evaporation, sputtering or other thin film deposition techniques known to the person of ordinary skill in the art. Other first layer alternatives include polymers, which may dissolve or depolymerize when an electric potential is applied or the local environment is changed. For example, many photoresists have high solubility in the presence of a high $OH^-$ concentration, which can be electrochemically generated locally around an electrode. Yet other alternatives include highly inert, conductive ceramics, such as tantalum nitride or titanium nitride, commonly used in integrated circuit fabrication, which can also be made to dissolve by electrochemical means.

Other metals having low reactivity may also be used. There is no requirement for dissolution or etch rate when activated, as this layer is typically fabricated as thin as necessary to ensure an impermeable seal with no regard for mechanical strength. The device also comprises a reference electrode (140), exposed to the environment (135) on the same side of the barrier (130). Layer (130) and electrode (140) are electrically connected (145) to a galvanic cell controller which produces the electric current at a specific potential range for barrier removal. If, for example, the device is fabricated on the silicon wafer of a complementary metal oxide semiconductor (CMOS) circuit, the galvanic cell controller can be built into the same substrate as the compartment and barriers. The exact potential, current, and waveform used by the galvanic cell controller depend on the nature of the barrier layer, but for most metals, including gold, the applied potential is positive with respect to the reference electrode (140). As understood by the person of ordinary skill in the art, in some instances it can be advantageous to use a third counter electrode adjacent to the reference electrode to improve the consistency of the process. This third electrode can be used with the barrier and reference electrodes in a configuration commonly referred to as a potentiostat. In some cases, for example with gold, dissolution can in certain circumstances be faster when the control output is cycled between different potential voltages at the expense of a higher energy consumption and increased device complexity, if additional speed is required. It can be noted that in the case of implantable medical devices, the electrochemical environment (135) may either be the human body, or the drug or sensor enclosed within the implant. In some cases, it may be preferable for the first barrier layer (130) to be on the side of the enclosed drug or implant, e.g. exchanged in place with barrier (125), as the chemistry of this environment may be better controlled and tuned to allow for the barrier layer to more readily dissolve when required. In these alternative embodiments, the internal barrier is dissolved first.

The second layer (115) of the barrier, protected by the first thin, electrically removable layer (130), can be a considerably less stable material which can spontaneously degrade in contact with the environment (135) with little or no power input. Magnesium is an example of such a material. For example, magnesium will spontaneously dissolve when exposed to water in the pH range normally found in the body. Alternatively, the second layer material can be used as part of a galvanic cell (battery). The difference in the cell potential of the two electrodes can cause dissolution at one of the electrodes. In this case, the electrolyte is the environment (135) on one side of the barrier, the anode is the second barrier layer (115), the cathode is another metal on the same device in contact with the environment, e.g. (150), and the load is an electrical connection between the anode and cathode. For example, magnesium can be used as the second layer, and its dissolution can be accelerated by being part of the galvanic cell. Other metals that would not normally dissolve in water can be made to dissolve by galvanic corrosion when part of a galvanic cell, as known to the person of ordinary skill in the art. The potential of the galvanic cell is analogous to the potential applied to gold to cause electrochemical dissolution. In some embodiments, the galvanic cell leading to an accelerated dissolution of the second layer could be formed with the other electrode being the first layer, that may not be completely removed and is still in contact with the second layer when the second layer becomes exposed to the electrochemical environment. Such a situation may occur if the first layer is gold and the second layer is magnesium. It can be noted that in some cases the reference electrode (140) for the first barrier layer (130) may be reused as the cathode to reduce complexity, obviating the need for a separate cathode (150). In this case, the cathode (150) is absent, and the electrical connection is added to reference electrode (140). It can be noted that the cell is only formed when the first barrier layer (130) is dissolved away, so this barrier layer (115), despite its reactivity, will remain intact until the first layer (130) seal is broken.

Because of its high or spontaneous reactivity once the first barrier layer is dissolved away, this second layer can be relatively thick, providing significant mechanical strength and protection. Another level of control may be obtained by replacing the permanent electrical connection between anode and cathode with an electrically controllable load that can further modulate how quickly or slowly this reaction proceeds. This may be useful in cases where the first barrier layer has some non-negligible degradation rate before activation. Additionally, this load may carry out other functions of the device. For example, the galvanic cell may also power transmitter circuitry or measurement circuitry. It can be noted that in implantable devices where the environment on one side of the barrier (135) is the human body, and the other side (120) is the drug or sensor being separated, it may be preferable to place the cathode of the battery on the side where the drug or sensor is being stored, as it permits better control over the electrolyte of the galvanic cell. In this case the cathode could be optionally placed such as (435) in FIG. 4. In FIG. 1, (105) illustrates a substrate which provides mechanical support for the barriers. In some embodiments, this substrate is made of silicon, silicon dioxide, or silicon nitride, all biocompatible materials frequently used in the fabrication of microscale devices.

In some embodiments, the second barrier layer (115) may be a material which spontaneously degrades when in contact with the environment (135) on one side of the barrier, and optionally also when in contact with the environment on the other side of the barrier (120). In general, the only requirement is that this reaction occurs quickly enough for the separation to no longer be present when desired, and that the material is sufficiently strong. Depending on the overall mechanical characteristics of the system, some water-soluble polymers, such as polyvinyl alcohol (PVA), may be sufficient to perform this function. Many metals also fulfill this function even without an attached load, such as, for example, magnesium, sodium, calcium, and most alkali and alkaline earth metals. Some materials, when fabricated with high internal mechanical stresses, will also spontaneously mechanically degrade in contact with a liquid. These materials include silicon nitride, silicon dioxide, and silicon. In these embodiments, degradation of the second barrier layer (115) may be classified as either "chemical" or "mechanical" in nature, but provide the same functionality.

There can optionally be a third barrier layer (125), immediately exposed to the environment (120) on the other side of the barrier, having similar criteria as the first barrier layer (130). Since the first layer (130) of the barrier is used to initiate removal of the second layer (115) of the barrier, there is no need for the third layer (125) to be electrically removable, as it would so thin that it would collapse without the support of the second layer. As such, a wider array of materials may be used for this third barrier layer (125), including, for example, silicon nitride, silicon oxide, silicon, and aluminum oxide. For example, a silicon nitride layer could be deposited using chemical vapor deposition techniques, and it could be patterned using lithographic and etching techniques known to the person of ordinary skill in the art. In medical devices where side (120) of the barrier contains either the drug to be delivered, or a biosensor membrane, this third barrier layer (125) may not always need to be present as the inner environment may be designed to be non-reactive towards the second barrier layer (as illustrated for example in FIG. 3). In some embodiments, the membrane or drug are lyophilized and are not in the liquid phase; therefore the third barrier (125) may not be necessary. Similarly, this third barrier can be made more inert to the contained compound than the second layer might be, as can also be the case for the other walls of the inner environment.

Targeted dissolution to specific areas of the external layers could also be accomplished. This could be done for example, by making use of the phenomena involved in crevice corrosion in an aqueous environment containing chloride. By forming a crevice, filled with fluid and electrolyte, over sections of a metal film that is elsewhere exposed to the electrochemical environment, the local chemical environment between the insulators and the metal film could become more acidic and less oxygenated than the external environment. Such a crevice can be formed, for example, by placing partially adhered insulators over regions of the metal film, so that fluid and electrolyte fill the gap between the two. The overlying layer could also be conductive, so long as the crevice is formed.

Figure 3:
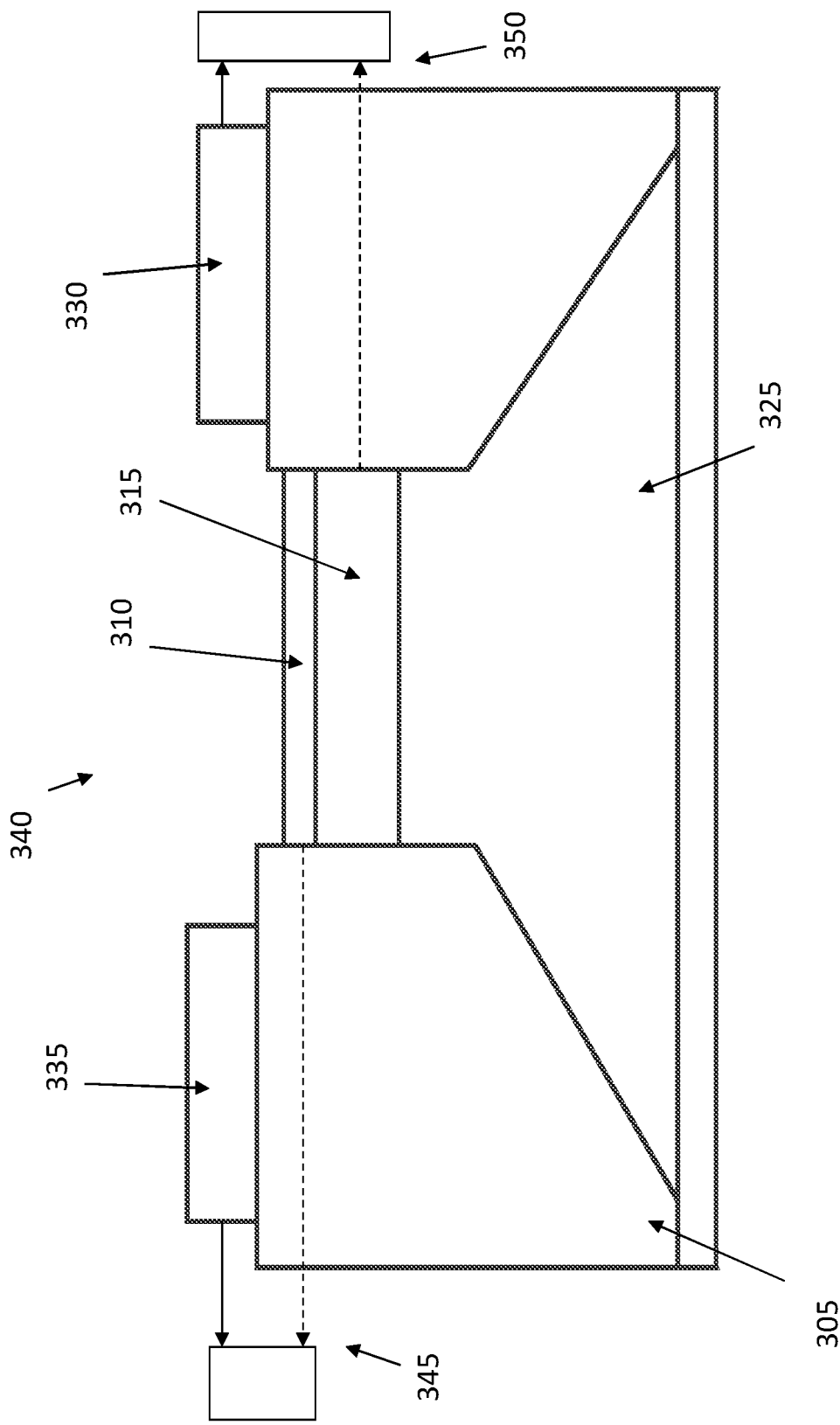
FIG. 3 illustrates an exemplary device comprising two barriers.
Figure 6:
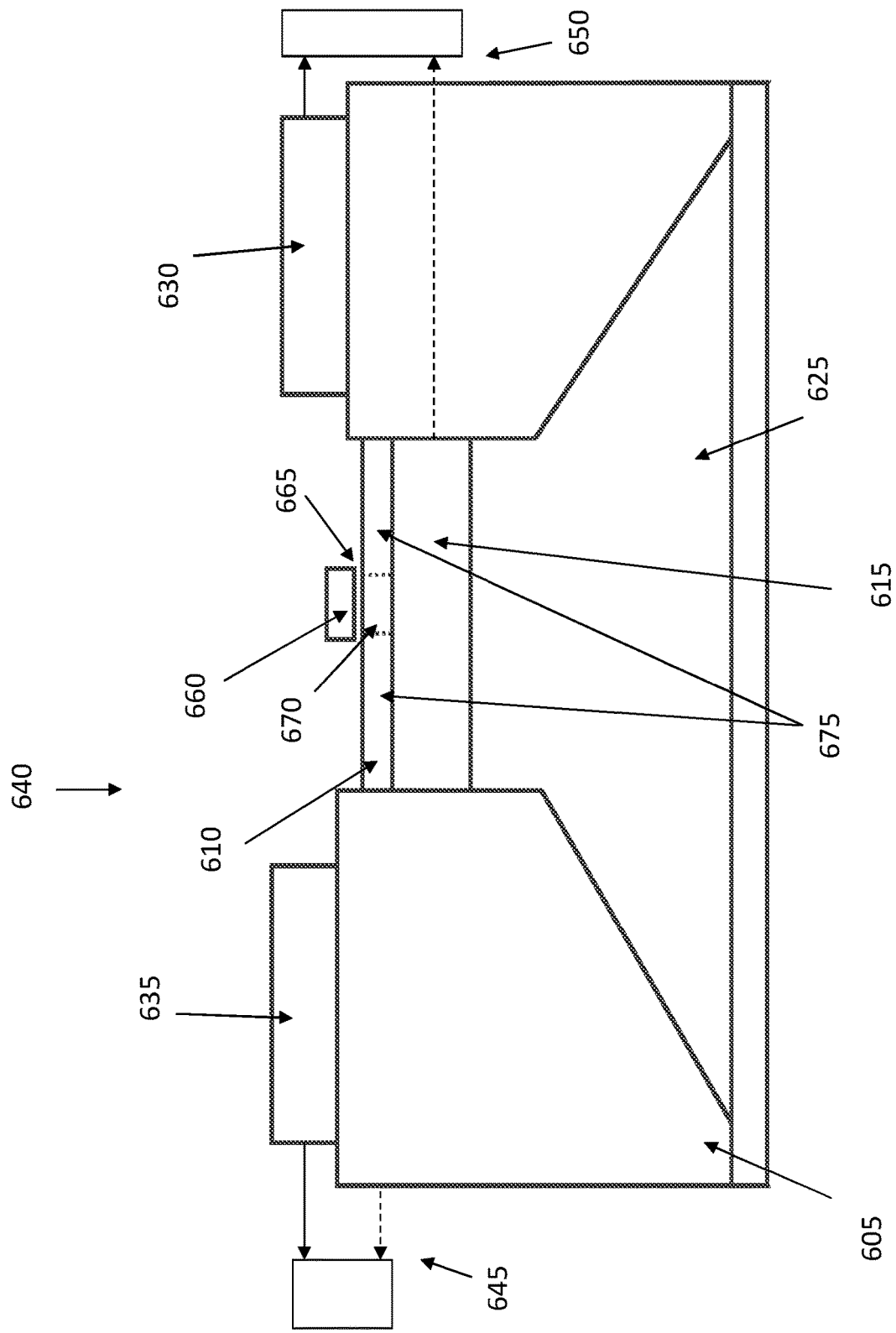
FIG. 6 illustrates a device comprising a targeted dissolution technique.

An embodiment of such a device is illustrated in FIG. 6, which is similar to the embodiment of the device in FIG. 3, but with the addition of a crevice based on the concept of targeted corrosion. In this embodiment, the crevice (665) is formed between the external seal layer (610) and an above layer of material (660) used for targeting, which is not completely adhered to the seal barrier (610). The portion of the seal layer (610) directly under the crevice (670) will preferentially dissolve and is in that sense targeted relative to the adjacent non-covered areas (675), by controlling the location of the above layer (660). In such an embodiment, the targeted region (670) could dissolve down to the spontaneously dissolving layer (615), exposing it to the external environment (640) sooner, or with less applied power than if the targeting material (660) had not been present and the seal layer had more uniformly dissolved across its exposed surface, as for the case of the seal layer (310) in FIG. 3. In FIG. 6, material (660) is shown as detached from the barrier (610) to clarify the presence of the exposed crevice; however, the material (660) can be attached to the barrier (610) at other locations. In this sense, the adhesion is partial as there are areas where the two layers (660,610) are attached and areas where the two layers are not attached.

For particular materials such as gold, this environment could cause a faster dissolution of the barrier material, relative to other areas of the film. The difference in the local chemical environments could cause an electrochemical concentration cell, so that the targeted regions would behave as anodes and the non-targeted regions as cathodes. This process commonly occurs in crevice corrosion. In this embodiment, some portion of the current that goes into dissolving the targeted anode regions would come from the non-targeted cathode regions, potentially reducing the total amount of current needed to be generated by the device, and therefore reducing the total power requirements. By causing the exposed regions to behave as cathodes, their dissolution, upon application of a potential, could be further reduced relative to the targeted regions, in a process similar to cathodic protection with sacrificial anodes. By increasing the size ratio of the cathodic to anodic regions, the current density in the targeted regions from the concentration cell could be increased, leading to a controllable increase in the rate of dissolution derived from the concentration cell. Applicable materials such as gold would also be stable under the insulator until a potential was applied, but preferentially degrade after the application of the electrical potential. Additionally, preferential dissolution of the film at grain boundaries could be modulated by controlling the grain structure of the films. Grain structure control of polycrystalline material is known to the person of ordinary skill in the art.

By making use of targeted dissolution, the second, spontaneously reactive layer could potentially be exposed to the external environment faster, or using less power than if the first layer was dissolving uniformly across the full surface, as less material would need to be dissolved to break the seal. By controlling the geometry of the targeted and non-targeted regions, specific patterns of weakening could be induced in the external layers in order, for example, to complement any built-in stresses in the film, and lead to seal rupture sooner, or with less power than if non-targeted dissolution was used. Subsequent and spontaneous breakdown of the underlying layer could then lead to a more uniform rupturing of the overlying seal layer, which was initially broken in a targeted manner. The spontaneous breakdown of the mechanically supporting layer may in general mitigate incomplete barrier opening due to non-uniform dissolution of the seal layer.

Figure 2:
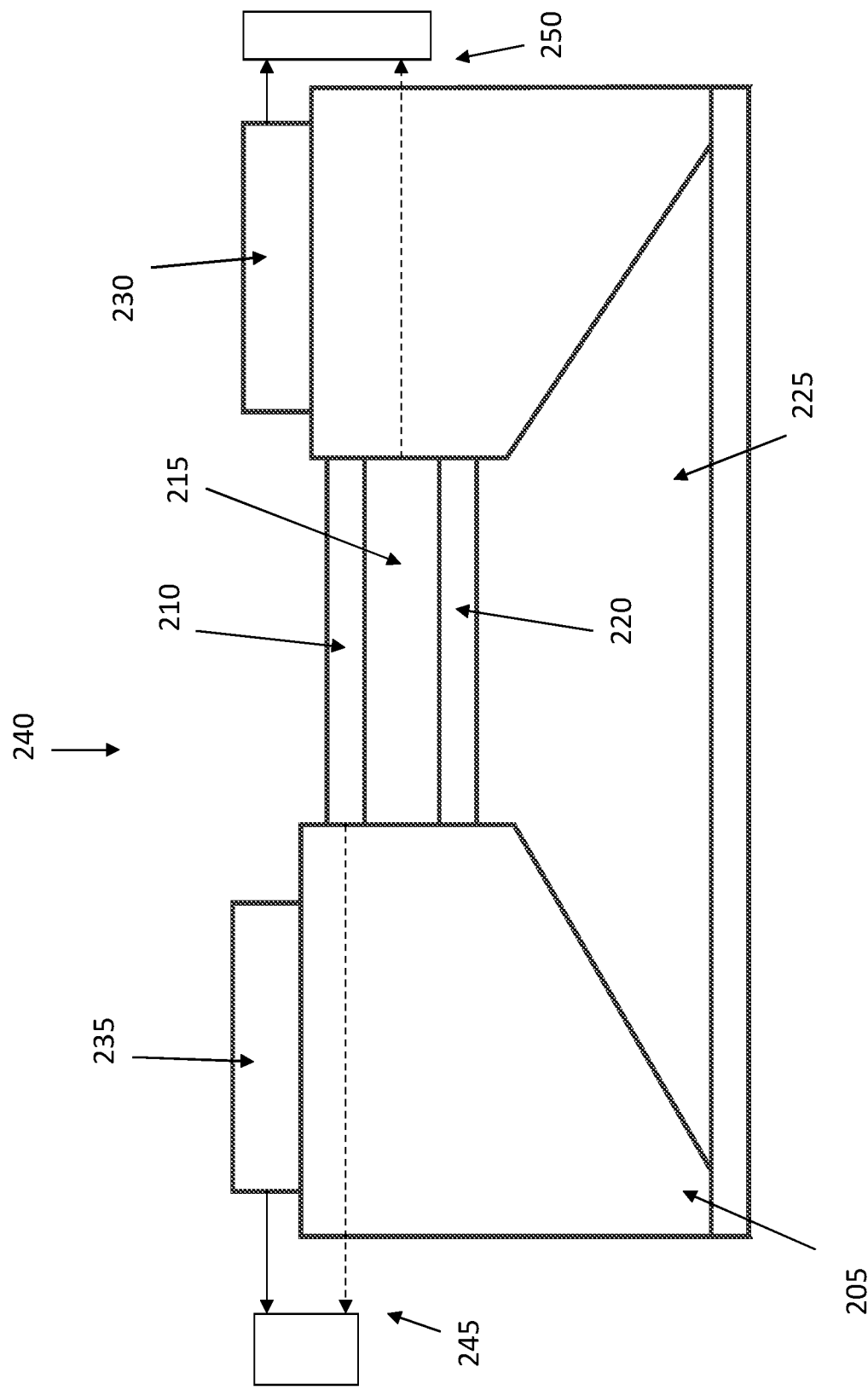
FIG. 2 illustrates an exemplary device comprising three barriers.

FIG. 2 illustrates an exemplary device according to the present disclosure. A substrate (205) may be shaped to contain a drug or biosensing material (225). For example in a silicon substrate, a directional or isotropic etch process can be used to create a cavity in the substrate. Other methods of forming a cavity in the substrate of interest are known to the person of ordinary skill in the art. In some embodiments such as a thin membrane biosensor, the sealed off compound may be thin enough that a shaped compartment is not necessary, and the barrier layers are formed over, and extend past, the compound in order to form a seal. The volume of the cavity and size of the opening can vary greatly depending on application, as this typically controls the dosage for drug delivery or sensitivity for biosensing applications. In some embodiments, the opening is usually less than 1 mm². In biosensing applications, such as glucose monitoring, the opening size can be, for example, from 50×50 micron or smaller to 500×500 micron or larger, depending on the required sensitivity. Two or, optionally, three barriers, (210), (215) and (220) may protect the drug (225) from the body environment (240), similarly as described in FIG. 1. For example, barrier (210) may be made of gold, while barrier (215) of magnesium, and optional barrier (220) of gold or platinum. In the case of using metal layers for each of these barrier, the outer barriers (210) and (220) can be relatively thin compared to the center barrier. For example, the outer barriers can be 50 nm thick or less. The center barrier is typically fairly thick, compared to the outer barriers, and sized depending on the strength required, given the size of the opening. For example, the center barrier may be 300 nm thick or more. In some embodiments, therefore, the center barrier is thicker than the outer barrier, for example by at least a factor of 5. In other embodiments, for example where the center barrier is a metal and the outer layer is a polymer, the center barrier may be thinner than the outer layer. The reference electrode (235) may comprise Pt or Ag/AgCl. Electrical connections (245) may enable signaling (235) and (210) to activate the barrier removal. The cathode (230) may be, for example, made of platinum. The cathode (230) and the barrier (215) may be electrically connected (250) to a galvanic cell controller or an energy harvesting unit. The environment (240) may naturally contain chloride ions.

FIG. 3 illustrates a device similar to that of FIG. 2, but without the optional barrier layer. A substrate (305) may be shaped so as to contain a lyophilized drug or biosensing material (325). Two barriers, (310), (315), may protect the drug (325) from the body environment (340), similarly as described in FIGS. 1 and 2. For example, barrier (310) may be made of gold, while barrier (215) of magnesium. Since the drug is lyophilized, or the sensor is dry, an optional third barrier may not be required. The reference electrode (335) may comprise Pt or Ag/AgCl. Electrical connections (345) may enable signaling (335) and (310) to activate the barrier removal. The cathode (330) may be, for example, made of platinum. The cathode (330) and the barrier (315) may be electrically connected (350) to a galvanic cell controller or an energy harvesting unit. The environment (340) may naturally contain chloride ions.

Figure 4:
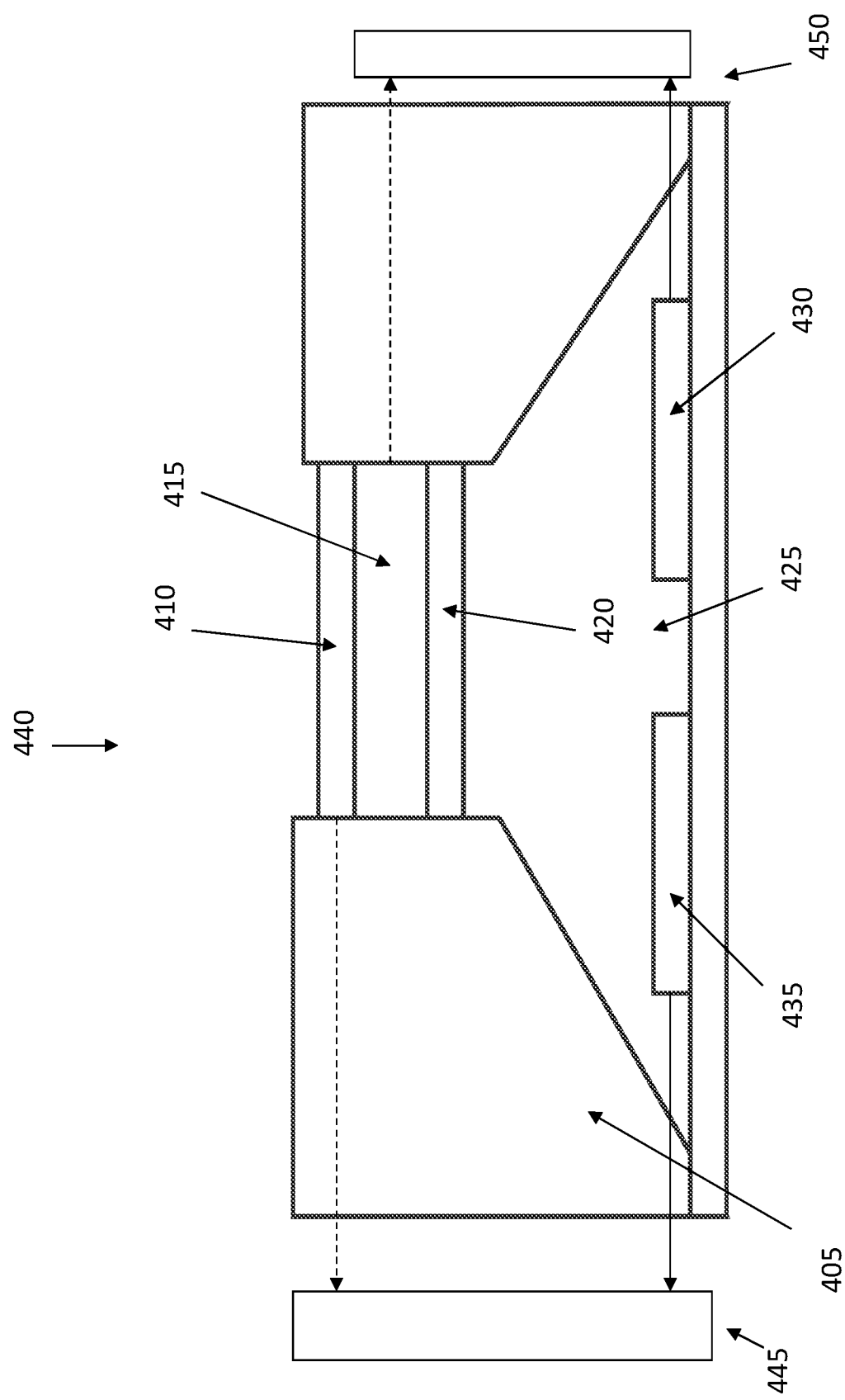
FIG. 4 illustrates an exemplary device comprising internal electrodes.

FIG. 4 illustrates an exemplary device according to the present disclosure. A substrate (405) may be shaped to contain a drug or biosensing material (425). The drug or biosensing material may be in the liquid phase, contain ions and support ions for a magnesium galvanic cell. Three barriers, (410), (415) and (420) may protect the drug (425) from the body environment (440) which contains unknown ion concentrations. For example, barrier (410) may be made of gold, platinum, silicon dioxide, silicon nitride, or aluminum oxide, while barrier (415) of magnesium, and barrier (420) of gold. The reference electrode (435) may be placed within the drug reservoir, and comprise Pt or Ag/AgCl. Electrical connections (445) may enable signaling (435) and (410) to activate the barrier removal. The cathode (430) may be, for example, made of platinum, and also be placed within the reservoir. In certain embodiments, the cathode and reference electrode can be the same electrode, with their function at any point in time determined by the device circuitry. The cathode (430) and the barrier (415) may be electrically connected (450) to a galvanic cell controller or an energy harvesting unit.

In medical devices where the inner environment can potentially be designed, electrical dissolution of the barrier may be initiated from the barrier layer in contact with the inner environment rather than the outer environment (human body). In other words, the inner environment may be, for example, a drug in a fluid which can be modified according to the dosing requirements as well as the barrier dissolution requirements. For example, gold membranes typically require sufficient chloride ions for fast dissolution. If the quantity inside the human body is insufficient, the drug being delivered may be formulated to have sufficient chloride ion to ensure fast dissolution. In some embodiments, the inner environment may be formulated to ensure fast dissolution of the membrane. The materials for the middle barrier layer may also be designed accordingly, possibly allowing for even faster opening of the barrier. Because the layer of the barrier exposed to the outer environment is so thin, it should mechanically tear or disintegrate once the middle layer has fully dissolved. Thus, in these embodiments, the outer environment layer only needs to be inert with respect to the outer environment. For example, an inert material, such as platinum, can protect the middle barrier layer from the outside environment. As illustrated in FIG. 4, in these embodiments the electrodes (435, 430) are located in the reservoir as the inner barrier (420) is the barrier being dissolved first, instead of the outer barrier (410). In these embodiments, the outer layers of the multilayer barrier are effectively chemically amplified by the inner layer, which provides the mechanical support for this highly efficient, electrically removable fluid barrier.

In certain applications, a structure such as that in FIG. 2 may lead to a first layer that does not dissolve into small enough particles before becoming isolated from the galvanic cell control circuit. This can happen if the first layer has excessive structural integrity, for example when made thick enough to ensure that lower layers are sealed from the environment. Additionally, this problem can occur if the underlying, spontaneously reacting layer dissolves away through a break in the first layer seal, and the first layer also breaks near the edges of the substrate cavity. This breaking pattern could lead to a partially intact first layer film that is not sufficiently electrically connected to the galvanic cell controller, and therefore cannot further be dissolved by it. To avoid such situations, additional, auxiliary layers between the first layer and the spontaneously dissolving second layer can be included. For example, an intermediate seal layer, that may be conductive and dissolves more slowly than the main spontaneously dissolving layer, may be used to allow for the first layer to sufficiently dissolve before losing electrical contact with the galvanic cell controller, and also before the main, spontaneously dissolving layer becomes exposed to the external environment.

A different embodiment of an auxiliary layer might be as a conductive and porous mesh of some material that may not dissolve or may dissolve relatively slowly in the environment. This mesh would remain in electrical contact with the galvanic cell controller for at least a sufficient period, after activation of the controlled opening of the barrier, so that the first seal layer can be sufficiently removed. For example, this mesh could be a film of platinum with a grid of openings, or a conductive and porous polymer. In the case of a platinum grid, for example, the film could be fabricated between the spontaneously dissolving layer and the controllable seal layer. For example, the spontaneously dissolving layer may be magnesium and the controllable seal layer may be gold. In this example, the openings in the platinum mesh would be so that, at some locations, the gold and magnesium would be in contact, and in others the platinum would be in between them. In this example, after application of an electrical potential to dissolve the gold layer has yielded a break in the seal to the magnesium, the magnesium may completely dissolve before the gold has sufficiently dissolved. The control signal can be continuously applied or reapplied, and the gold layer would continue to dissolve anywhere it is connected to platinum, as the platinum mesh would remain connected to the galvanic cell controller. In some cases, the gold barrier directly above the magnesium layer, instead of the platinum layer, may be only partially dissolved before becoming separated from the platinum grid, and therefore the galvanic cell controller. To obviate this potential problem, the opening size in the platinum grid can be selected to yield sufficiently small particles of gold. In an embodiment with a platinum grid, the platinum mesh may remain intact for the duration of use of the device after the barrier is removed. In the case of a drug release device, the drug would flow out through the openings in the grid, whereas for a biosensor the sensor would no longer be isolated form the biologically relevant parameters of the external environment because of the openings in the grid. Such an embodiment may function similarly if the auxiliary platinum grid was instead located on the electrochemical side of the seal layer.

Another embodiment of the device may include an external auxiliary layer which reduces the impact of the immune response to the device. Such an auxiliary layer may, in some embodiments, be porous, and may be permanent in order to still allow breakdown of the underlying barrier layers and access to the compartment. However, the auxiliary layer would have a relatively reduced immune response compared to the barrier materials, or the contents of the compartment. A reduced immune response could lead to thinner capsule formation between the barrier and the implant tissue, so that transport of compounds through this capsule would be faster. In turn, this could, for example, improve the sensitivity and speed in biosensor applications and reduce the time for released drugs to spread out from the device, in drug release applications. Alternatively or in addition, such layers could elute compounds such as vessel endothelial growth factor, which could improve the blood flow through the local implant region, which may improve sensing or drug release properties. For example, the eluted compounds may increase the local oxygen concentration in biosensor applications, where low oxygen concentration prevents accurate measurement, as will be known to with the person of ordinary skill in the art. The compartment, container, or non-external, auxiliary layer part of the barrier structure could, in addition, contain a drug, counteracting an immune response, to be released into the area around the implant during the barrier breakdown process. For example, collagenase, if released from the device, could reduce the density of the capsule around the implant, so that transport of compounds through the thinned capsule would be faster.

An embodiment of barrier layers including auxiliary layers could still be relatively efficient compared to a device using only the controllably removable seal layer, and not the spontaneously dissolving layer, since the thickness needed for the controllably dissolving layer to ensure a seal between the external and internal environments could be thinner than that needed to form a mechanically stable seal without the underlying, spontaneously dissolving layer. Such concepts may also be applied if the layer adjacent to the internal compartment is the layer meant to controllably become unsealed, instead of, or in addition to, the layer adjacent to the external environment.

The present disclosure describes a device comprising a barrier which may be controllably removed with a low power electrical signal. The device and the barrier are resilient to chemical degradation by its surroundings, and designed to keep two environments separate (including gases, liquids, and chambers containing solids). The two environments typically refer to the human body, and a device inner environment, for example containing a drug.

In some embodiments, the device comprises: a first barrier layer, highly inert towards the environment on the external side of the barrier, which can be controllably removed at any time by an electrical signal; a second barrier, thicker than the first barrier and capable of providing mechanical support, composed of a material which is spontaneously reactive, can be readily made to be spontaneously reactive to the environment on the first side of the membrane, or is inherently permeable to the two environments; an optional third barrier, highly inert towards the environment on the internal side of the barrier, thin enough to collapse without the support of other barrier, and which can optionally be removed by an electrical signal. Additional layers with particular mechanical stress, permeability or dissolution properties may also be included in some embodiments.

In some embodiments, the first barrier is made of gold, and actuation occurs by electrochemical dissolution of gold. In some embodiments: the first barrier is a metal, and actuation occurs by electrothermal destruction of that barrier; the second barrier may be a thermal insulator, either reactive to the outside environment, or permeable to one or both of the two environments. In some embodiments, the center barrier is a part of a galvanic cell, and is composed of a reactive anodic material such as magnesium. Spontaneous removal of the barrier occurs when the galvanic cell is connected and the center barrier is exposed to one of the two environments.

In some embodiments, the third barrier is made of platinum or another noble metal. In some embodiments, one environment is a biological environment external to an implant for an organism, and the other environment contains drugs, a limited lifetime bio sensor, or other component of the implant requiring controlled exposure to the environment.

In some embodiments, the non-biological environment is engineered to support dissolution of the first and second layers to permit efficient removal of the membrane regardless of the condition of the biological environment. In some embodiments, the two environments are chemistries reactive to each other and kept separate until required.

In some embodiments, the device described herein can be used for non-biological applications in non-biological environments. A device as illustrated in FIG. 3 could, for example, be used where the external environment (340) is sea water, brine, an industrial process fluid or some other conductive, aqueous fluid. Another embodiment of the device as in FIG. 4 could alternatively be used in dry environments (440), as the electrochemical reaction would occur within the compartment (425).

Therefore, in some embodiments, the device is configured to contain a compound, such as a drug, or a biosensing compound, in liquid, solid or gaseous form, and have an opening to access the compound, the opening being blocked by the barriers described in the present disclosure, which can be removed according to the different methods described. The device, in some embodiment, comprises one or more containers, having at least one opening, the opening closed by removable barriers as described in the present disclosure. In the present disclosure, a "container" is intended as a part of the device as defining an inner volume which contains a compound such as a drug, a biosensing compound, in liquid, solid or gaseous form. The container has an opening closed by barriers as described in the present disclosure. For example, in FIG. 4 the container defines the inner volume containing (425). An example of an application of such a device is a long-lifetime, continuous-monitoring glucose sensor, which continually reports an accurate measurement of blood glucose. In these embodiments, each container contains a full glucose sensor, which includes a diffusion barrier, glucose oxidase or equivalent enzyme, and an electrochemical sensor. This type of sensor and variations on this sensor are known to the person of ordinary skill in the art. After any initial immune reaction to the implantation of such a device, the first compartment in such a device may be opened by electrically removing the barrier to that compartment. After the lifetime of the glucose sensor in this particular container has been exhausted, the barrier to the following container can be electrically removed and the next sensor can be used for measurement. In this way, the total lifetime of a continuous glucose monitoring device per implantation can be multiplied, limited by the size of the implant. In some embodiments, this device comprising multiple containers and their respective barriers is equivalent to a single device arranged in parallel, for example in a planar two-dimensional array. In some embodiments, one or multiple compartments can be opened at each dosing in order for a single implanted device to control both the duration between, and total volume of, drug released at each dose.

Figure 5:
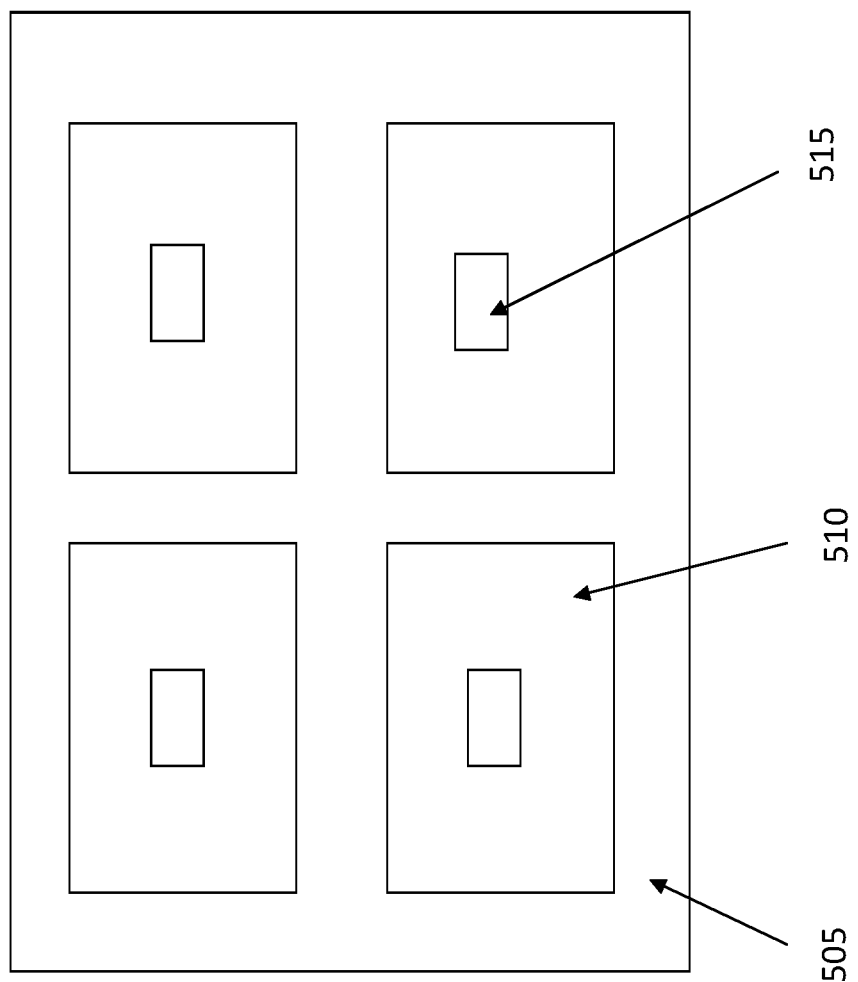
FIG. 5 illustrates an arrayed device comprising multiple containers and barriers.

FIG. 5 illustrates an exemplary arrayed device (505), which comprises, for example, four different sensors (510), each sensor as described above in the present disclosure. Each sensor comprises one or more barriers (515) that can be activated independently from adjacent devices of the array. In this embodiment, the array (505) is implanted in one procedure, and is effectively equivalent to the implantation of four different devices carried out at subsequent time. Therefore, for a small increase in the size of the implant, the number of implantation procedures, which can cause discomfort, financial cost, inconvenience and risk to the patient, can be reduced.

In the present disclosure, the functional layers or barriers of the device are referred to by a variety of terms as relevant within the context of this disclosure and the described embodiment. In general, there is a "first", "external" or "seal" layer which comprises a stable face of the barrier structure, which can be controllably degraded or broken by electrochemical or electrothermal means. In some embodiments, this layer may be facing the external environment and in others it may be facing the internal compartment. In some embodiments there may be additional auxiliary layers between this layer and the environment against which it forms a barrier, and in this sense "first" refers to it within the context of a device without auxiliary layers.

The "second", "center", or "spontaneous" layer generally refers to the layer that, upon the "seal" layer being broken, will eventually come into contact with an environment in which it will breakdown spontaneously or with low power requirements. This layer generally provides the mechanical stability of the barrier structure, such that after it breaks down the barrier structure should no longer separate the internal compartment from the external environment. In an embodiment only consisting of the "seal" and "spontaneous" layers, this would be the "second" layer. In some embodiments including auxiliary layers, this layer may then not be the second from the environment closest to the controllable "seal" layer.

In certain embodiments there may also be a "third" layer, which generally refers to a layer on the opposite side of the "spontaneous" layer from the "seal" layer and is in certain embodiments meant to prevent the "spontaneous" layer from degrading before controllably coming into contact with the environment separated from it by the "seal" layer. Such a layer is necessary in embodiments where the spontaneous layer could degrade when in contact with either the internal compartment or external environment. Such a layer is generally necessary when the contents of the internal compartment would not remain stably stored if in contact with the "spontaneous" layer, and the "seal" layer is closest to the external environment. Such a layer generally does not need itself to be actuated, and is made thin enough such that it mechanically falls apart when the "spontaneous" layer breaks down.

"Auxiliary" layers generally refer to additional layers besides these "seal", "spontaneous" and "third" types. These layers may not necessarily form sealed barriers, and may not necessarily degrade after controllable opening of the "seal" and overall barrier structure.

In the present disclosure, "electrothermal" dissolution refers to the process by which a metal layer becomes permeable or falls apart due to thermal damage caused by heating due to the application of an electric current. This type of barrier is therefore configured to "electrothermally" dissolve. When the barrier, such as the second barrier in some embodiments, will spontaneously dissolve upon contact with the surrounding chemistry, such barrier can be referred to as "chemically" dissolving. When the barrier, such as the first barrier in some embodiments, will dissolve upon application of a potential relative to a reference electrode when both are in electrical contact with the surrounding chemistry, such a barrier can be referred to as "electrochemically" dissolving. This terminology allows a clear distinction between the barriers that will dissolve upon application of a current meant to generate heat, for example from an energy storage unit within the device, and the barriers that will dissolve by the chemical reaction that occurs between the material of the barrier and the surrounding materials, for example a human body or aqueous environment containing chloride ions. Additionally, other barriers may be thin enough so as to "mechanically" break when the other supporting barriers are removed. These barriers can be referred to as breaking "mechanically".

In the present disclosure, it is to be understood that in certain embodiments of the electrochemical and electrothermal devices, the electric current is the functional parameter controlled in the signal form the device control systems, and in other applications it is the electric potential. Terms such as "control system", "galvanic cell controller" and "energy harvester" refer in general to possible functionality of such a device's control system, and are not meant to restrict or dictate the functionality of all possible embodiments of the device. Such a control system may not necessarily entirely reside on the same substrate as the device. Use of the term "signal", "electric potential" and "electric current" are meant generally to refer to the actuation imposed on the actuated components of the barrier structure and not to necessarily restrict the embodiment of such actuation, for example, in regard to electric potential values, time duration, and variations of the signal over time.

In the present disclosure "human body" is not meant to be limited to the species *Homo sapiens* and generally is understood to refer to the body and local environment of any biological organism. "Implant" is not limited to placement within a certain set of tissues of an organism and generally refers to a location anywhere within or near the biological organism pertinent for measuring relevant biological parameters. This, for example, includes locations within the subcutaneous space of a rodent, the digestive tract of a bird, among or within the food of an invertebrate or vertebrate, upon the skin or clothing of a human, within a petri dish for the growth of bacteria, within stored meat intended for future consumption, and within the fruit of a plant. The "chemical compounds" and/or "biological materials" contained within the sealed compartment of the device is to be generally understood as to also include viable and non-viable organisms such as for example lyophilized yeast or inactivated viruses.

Therefore, as described above, the present disclosure describes devices which, in some embodiments, have two or three barriers. In some embodiments, the initiating layer, or the barrier which initiates dissolution or breakage of all barriers and ultimately contact between the inner container of the sensor and the outer environment, is always electrochemically removed. At a positive voltage (e.g. around 1.2 V versus a saturated calomel reference electrode), the gold layer starts dissolving away electrochemically at very low power (typically with a current less than 1 microAmpere, therefore a power less than 1 microWatt). The amount of electrical power from such a low voltage source dissipated by the current, typically being less than 1 microAmpere for an exposed layer of less than $0.01$ $mm^2$ in area, is far too low to cause any thermal damage in a typical thermal environment, therefore all of the removal is electrochemical. However, in embodiments where the barrier is sufficiently thin, after any etched crack to a spontaneously dissolving underlying layer such as magnesium layer occurs, the rest of the barrier falls apart very quickly and without further applied power from the device. A problem with commercialized electrochemical removal methods is insufficient consistency in opening these membranes, and very high variance in opening time. Both of these problems are solved by the method described in the present disclosure.

In some embodiments, a different electrothermal technique can be employed. If the stable barrier to be electrothermally broken is very thin, electrothermal techniques can also be more efficient by using spontaneously dissolving underlying layers. Therefore, practically efficient electrothermal devices become possible by using a two or three layer barrier stack. The initiating layer is much thinner than what is normally used for electrothermal applications, and no longer has to be completely vaporized, since any small crack or damage will cause the inner layer to chemically degrade. Therefore, the power consumption is also much lower than in devices not using such an inner layer. In some embodiments, the chemical compound contained by the device can be a fluid, electrolyte, or solid electrolyte. In some embodiments, one or more of the barriers of a device may comprise an auxiliary compound configured to reduce an immune response from the organism, thereby increasing the effect of the drugs, or reducing adverse reactions due to the foreign body being implanted within the organism. For example, one of the barriers may comprise a polymer, and the auxiliary compound may be infused within the polymer, coming into contact with the organism adjacent to the polymer. The auxiliary compound may also aid in the dissolution of a barrier. In some embodiments, the auxiliary compound may both aid the dissolution of the barrier and reduce the immune response of the organism. For example, the auxiliary compound may comprise two compounds, one configured to aid in the dissolution of the barrier and another configured to reduce the immune response of the organism. In the present disclosure "unseal" refers to the barrier electrochemically dissolving, or mechanically degrading and breaking, or electrothermally melting. Therefore, the barriers can be referred to as unsealing when they allow passage of a compound as described in the present disclosure. The barriers can become entirely unsealed, or they may be partially unsealed if portions of the barrier remain in the device while allowing passage of the compound such as the fluids. In some embodiments, the auxiliary layer can protect the inner compound within the device. For example, during barrier dissolution, the pH of the environment may change. The pH change may damage the compound. The protective layer can be designed to degrade more slowly than other barrier layers, allowing the pH to slowly equilibrate in the environment, and protecting the compound from damage.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually. It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A device comprising:
   a container having an opening;
   a plurality of barriers closing the opening;
   a chemical compound or biological material within the container,
   wherein:
      the device is configured to be implantable within a human body or other organism,
      the plurality of barriers are configured to electrochemically or electrothermally unseal, upon application of an electric potential or current to at least one barrier of the plurality of barriers, thereby allowing interaction between the chemical compound or biological material and the human body or other organism;
   a reference electrode on an external surface of the device, thereby being in contact with the human body or other organism upon implantation of the device, wherein the reference electrode is electrically connected to a first barrier through a control circuit, wherein: the plurality of barriers comprises the first barrier, and the first barrier is not reactive to the human body or other organism and is configured to electrochemically unseal when the electric potential is applied to the first barrier;
   wherein the plurality of barriers comprises a second barrier configured to electrochemically or mechanically unseal upon contact with the human body or other organism, wherein the second barrier is placed between the first barrier and the chemical compound or biological material; and
   a cathode electrode on an external surface of the device, thereby being in contact with the human body or other organism upon implantation of the device, wherein the cathode electrode is electrically connected to the second barrier through a control circuit.

2. The device of claim 1, wherein the chemical compound or biological material comprises at least one of: a drug, a biosensing material.

3. The device of claim 1, further comprising a counter electrode on an external surface of the device, thereby being in contact with the human body or other organism upon implantation of the device, wherein the counter electrode is electrically connected to the first barrier and reference electrode through a control circuit.

4. The device of claim 3, wherein the counter electrode is made of a material comprising at least one of: Pt, and C.

5. The device of claim 1, wherein the first barrier comprises at least one of: gold, electrochemically degrading materials, and a polymer.

6. The device of claim 1, wherein, upon contact with the human body, the second barrier electrochemically or mechanically unseals with no additional power dissipation by the device.

7. The device of claim 1, wherein the second barrier comprises magnesium.

8. The device of claim 1, wherein the plurality of barriers further comprises an auxiliary compound configured to facilitate dissolution of the first barrier.

9. The device of claim 1, wherein the plurality of barriers further comprises an auxiliary barrier placed between the second barrier and the compartment, wherein the auxiliary barrier is configured to protect the chemical compound or biological material within the container.

10. The device of claim 1, wherein the plurality of barriers further comprises an auxiliary layer, wherein the auxiliary layer is configured to reduce an immune response to the device upon implantation in the human body or other organism.

11. The device of claim 1, further comprising a galvanic cell controller or an energy harvesting unit, the galvanic cell controller or the energy harvesting unit being electrically connected to the cathode electrode and to the second barrier.

12. The device of claim 1, wherein the applied electric current is less than one microAmpere and an area of a barrier of the plurality of barriers is smaller than $0.01$ $mm^2$.

13. The device of claim 1, wherein at least one region of the first barrier is configured to be individually targeted for electrochemical dissolution.

14. The device of claim 13, wherein the at least one region is a crevice configured to dissolve at a rate higher than remaining areas of the first barrier.

15. The device of claim 13, wherein the at least one region is a grain boundary.

16. The device of claim 1, wherein the reference electrode comprises at least one of: Pt, and Ag/AgCl.

17. A device comprising:
   a container having an opening;
   a plurality of barriers closing the opening;
   a chemical compound or biological material within the container, wherein:
      the device is configured to be implantable within a human body or other organism,
      the plurality of barriers are configured to electrochemically or electrothermally unseal upon application of an electric potential or current to at least one barrier of the plurality of barriers, thereby allowing interaction between the chemical compound or biological material and the human body or other organism;
   a reference electrode on an external surface of the device, thereby being in contact with the human body or other organism upon implantation of the device, wherein the reference electrode is electrically connected to a first barrier through a control circuit; wherein: the plurality of barriers comprises the first barrier, and the first barrier is not reactive to the human body or other organism and is configured to electrochemically unseal when the electric potential is applied to the first barrier; wherein the plurality of barriers comprises a second barrier configured to electrochemically or mechanically unseal upon contact with the human body or other organism, wherein the second barrier is placed between the first barrier and the chemical compound or biological material, wherein the plurality of barriers comprises a third barrier placed between the second barrier and the chemical compound or biological material, wherein the third barrier is not reactive to the chemical compound or biological material and is configured to mechanically break upon dissolution of the second barrier.

18. The device of claim 17, wherein the third barrier comprises at least one of: gold, platinum, silicon dioxide, silicon nitride, silicon, titanium nitride, tantalum nitride, and aluminum oxide.

19. The device of claim 17, further comprising a cathode electrode within the container, thereby being in contact with the chemical compound, wherein the cathode electrode is electrically connected to the second barrier.

20. A system comprising an array of devices, each device of the array of devices as described in claim 1, wherein the system is configured to unseal the plurality of barriers of any one device of the array of devices, independently from adjacent devices of the array of devices, by means of electrochemical or electrothermal dissolution.

21. A device comprising:
a container having an opening;
a plurality of barriers closing the opening;
a chemical compound or biological material within the container,
wherein:
the device is configured to be implantable within a human body or other organism,
the plurality of barriers are configured to electrochemically or electrothermally unseal upon application of an electric potential or current to at least one barrier of the plurality of barriers, thereby allowing interaction between the chemical compound or biological material and the human body or other organism;
a reference electrode on an external surface of the device, thereby being in contact with the human body or other organism upon implantation of the device, wherein the reference electrode is electrically connected to a first barrier through a control circuit, wherein: the plurality of barriers comprises the first barrier, and the first barrier is not reactive to the human body or other organism and is configured to electrochemically unseal when the electric potential is applied to the first barrier;
wherein the plurality of barriers comprises a second barrier configured to electrochemically or mechanically unseal upon contact with the human body or other organism, wherein the second barrier is placed between the first barrier and the chemical compound or biological material; and
a cathode electrode on an external surface of the device, thereby being in contact with the human body or other organism upon implantation of the device, wherein the cathode electrode is electrically connected to the second barrier through a control circuit; and
the plurality of barriers comprises a third barrier placed between the second barrier and the chemical compound or biological material, wherein the third barrier is not reactive to the chemical compound or biological material and is configured to mechanically break upon dissolution of the second barrier.

* * * * *